United States Patent
Siddu et al.

(10) Patent No.: US 7,299,697 B2
(45) Date of Patent: Nov. 27, 2007

(54) METHOD AND SYSTEM FOR INSPECTING OBJECTS USING ULTRASOUND SCAN DATA

(75) Inventors: Dinesh Mysore Siddu, Bangalore (IN); Sandeep Kumar Dewangan, Bangalore (IN); Gopichand Katragadda, Bangalore (IN); Sivaramanivas Ramaswamy, Bangalore (IN)

(73) Assignee: General Electric Company, Schenectady, NY (US)

( * ) Notice: Subject to any disclaimer, the term of this patent is extended or adjusted under 35 U.S.C. 154(b) by 147 days.

(21) Appl. No.: 11/094,909

(22) Filed: Mar. 31, 2005

(65) Prior Publication Data

US 2006/0219011 A1 Oct. 5, 2006

(51) Int. Cl.
*G01N 29/11* (2006.01)

(52) U.S. Cl. .......................... 73/597; 73/587; 73/599; 73/602; 73/799

(58) Field of Classification Search .................. 73/597, 73/599, 600, 602, 587, 579, 618, 627, 628, 73/629, 778, 799, 801, 620, 623
See application file for complete search history.

(56) References Cited

U.S. PATENT DOCUMENTS

| | | | | |
|---|---|---|---|---|
| 3,766,775 A * | 10/1973 | Gunkel | ........................ | 73/623 |
| 4,382,383 A * | 5/1983 | de Buda et al. | .............. | 73/592 |
| 5,189,915 A * | 3/1993 | Reinhart et al. | .............. | 73/623 |
| 5,280,723 A * | 1/1994 | Aharoni et al. | ............... | 73/602 |
| 5,392,652 A * | 2/1995 | Levesque et al. | ............. | 73/629 |
| 5,511,425 A * | 4/1996 | Kleinert et al. | ............... | 73/627 |
| 5,675,084 A | 10/1997 | Goedecke | ..................... | 73/623 |
| 5,804,730 A * | 9/1998 | Pfannenstiel et al. | ......... | 73/622 |
| 6,243,657 B1 | 6/2001 | Tuck et al. | .................. | 702/150 |
| 6,553,837 B1 * | 4/2003 | Lysen | .......................... | 73/579 |
| 6,571,634 B1 * | 6/2003 | Bazarov et al. | .............. | 73/623 |
| 6,578,422 B2 * | 6/2003 | Lam et al. | .................... | 73/622 |
| 6,745,136 B2 * | 6/2004 | Lam et al. | .................... | 702/54 |
| 6,748,808 B2 * | 6/2004 | Lam et al. | .................... | 73/622 |
| 6,802,221 B2 * | 10/2004 | Hedeen et al. | ................ | 73/587 |
| 6,848,313 B2 * | 2/2005 | Krieg et al. | .................. | 73/628 |
| 7,082,833 B2 * | 8/2006 | Heyman et al. | ............... | 73/598 |
| 2003/0136195 A1 | 7/2003 | Krieg et al. | .................. | 73/628 |
| 2006/0137451 A1 * | 6/2006 | Dewangan et al. | ........... | 73/579 |

FOREIGN PATENT DOCUMENTS

GB 2380794 A 4/2003
WO WO 03/021249 A2 3/2003

* cited by examiner

*Primary Examiner*—Hezron Williams
*Assistant Examiner*—Jacques M. Saint-Surin
(74) *Attorney, Agent, or Firm*—Fletcher Yoder

(57) ABSTRACT

A method and apparatus for estimating a depth of a crack from ultrasound scan data are provided. The method includes mapping multiple amplitude responses from the ultrasound scan data, each mapped amplitude response being representative of a signal from one of the sensors. The method further includes locating multiple linear responses among the mapped amplitude responses, each linear response being an indicator of a reflected signal from the crack. One or more sensor that corresponds to the linear responses from a given crack is identified. The depth of the crack is estimated using data from the identified sensors.

16 Claims, 3 Drawing Sheets

METHOD AND SYSTEM FOR INSPECTING OBJECTS USING ULTRASOUND SCAN DATA

BACKGROUND

The invention relates generally to inspection systems and particularly to pipeline inspection systems that use ultrasound data for detecting and sizing cracks and notches in pipelines.

Pipelines that allow a large amount of material to be transported from one place to another are widely used in a variety of industries. A variety of fluids such as oil and/or gas are transported cheaply and efficiently using pipelines. Particulate matter, and other small solids suspended in fluids may also be transported through pipelines. Underground and underwater (deep sea) pipelines typically carry enormous quantities of oil and gas products that are important to energy-related industries, often under extreme conditions such as high pressure, high (or low) temperature and high flow rate.

Flaws in constituent pipes may cause pipeline integrity degradation as the pipeline infrastructure ages. Corrosion or other pipeline defects can be caused by small spots of weakness, subsidence of the soil, local construction projects, seismic activity, weather, wear and tear caused by normal use, and the like. Accordingly, potential defects and anomalies can appear on the surface of the pipeline in the form of corrosion, mechanical damage, fatigue cracks, stress corrosion cracks, hydrogen-induced cracks, or distortion because of dents or wrinkles.

Maintaining and protecting existing pipeline networks is proving to be a challenge. Current state-of-art inline inspection systems use Pipeline Inspection Gages (PIG). PIGs move through a section of pipeline to acquire data from multiple sensors. A typical single run for the PIG may be more than 100 km long. The process of analyzing data obtained from the PIG and making practical use of the analysis is often burdensome. There are a variety of PIGs, common ones are the magnetic flux leakage PIGs used for corrosion detection and ultrasound PIGs used for crack detection. Current data analysis methods require on an average, about 200 man-days using ultrasound crack detection techniques to analyze and evaluate data from a 100 km long pipeline section.

Accurate sizing of the flaws (for example, cracks and the like) plays an important role in assessing the impact and severity of pipeline defects. Without accurate information regarding flaw size, it may be difficult to rate the quality of the pipeline or perform any remaining life estimation studies for such objects. Manual crack sizing leads to subjectivity and operator dependence, which in turn, might lead to inconsistent sizing estimates.

Ultrasonic non-destructive evaluation (NDE) methods for estimation of crack sizes in PIG based pipeline inspection include echo amplitude drop, and use of a distance-amplitude-correction curve. Most of these techniques involve assessment of reflection amplitude and acoustic shadow information by manual means. The use of amplitude data alone may not be reliable when trying to identify cracks or crack-like flaws, since the amplitude of the reflected sound signal depends on shape, size, type, orientation and position of the crack or crack-like flaw.

Therefore, there is a need for an improved technique for accurately estimating depth of cracks in pipelines and similar objects to facilitate effective repair and maintenance follow-up action.

BRIEF DESCRIPTION

Briefly in accordance with one aspect of the present technique, a method for estimating a depth of a crack from ultrasound scan data is provided. The method utilizes circumferentially distributed ultrasound sensor array for obtaining crack sizing. The method includes mapping multiple amplitude responses from the ultrasound scan data (B-scan), each mapped amplitude response being representative of a signal from one of the sensors. The method further includes locating multiple linear responses among the mapped amplitude responses, each linear response being an indicator of a reflected signal from the crack. The linear responses corresponding to a particular crack (reflector) are identified, and the depth of the crack is estimated using data from the idenified sensors.

In accordance with another aspect, an apparatus for estimating a depth of a crack from ultrasound scan data is provided. The apparatus includes an amplitude processor that is adapted to map multiple amplitude responses from the ultrasound scan data, and to locate multiple linear responses. Each mapped amplitude response is representative of a respective sensor signal, and each linear response is an indicator of a reflected signal from the crack. The apparatus further includes a crack sizing component that is adapted to identify respective sensors corresponding to respective linear responses and to estimate the depth of the crack using data from the respective sensors.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The various aspects of the present technique deal with identifying and estimating the depth of cracks and crack-like flaws in objects. Though the aspects have been described in relation to pipeline applications, the techniques described herein are equally applicable in other environments, for example, estimating the depth of cracks and crack-like flaws in rail tracks or in plates or bars.

Figure 1:
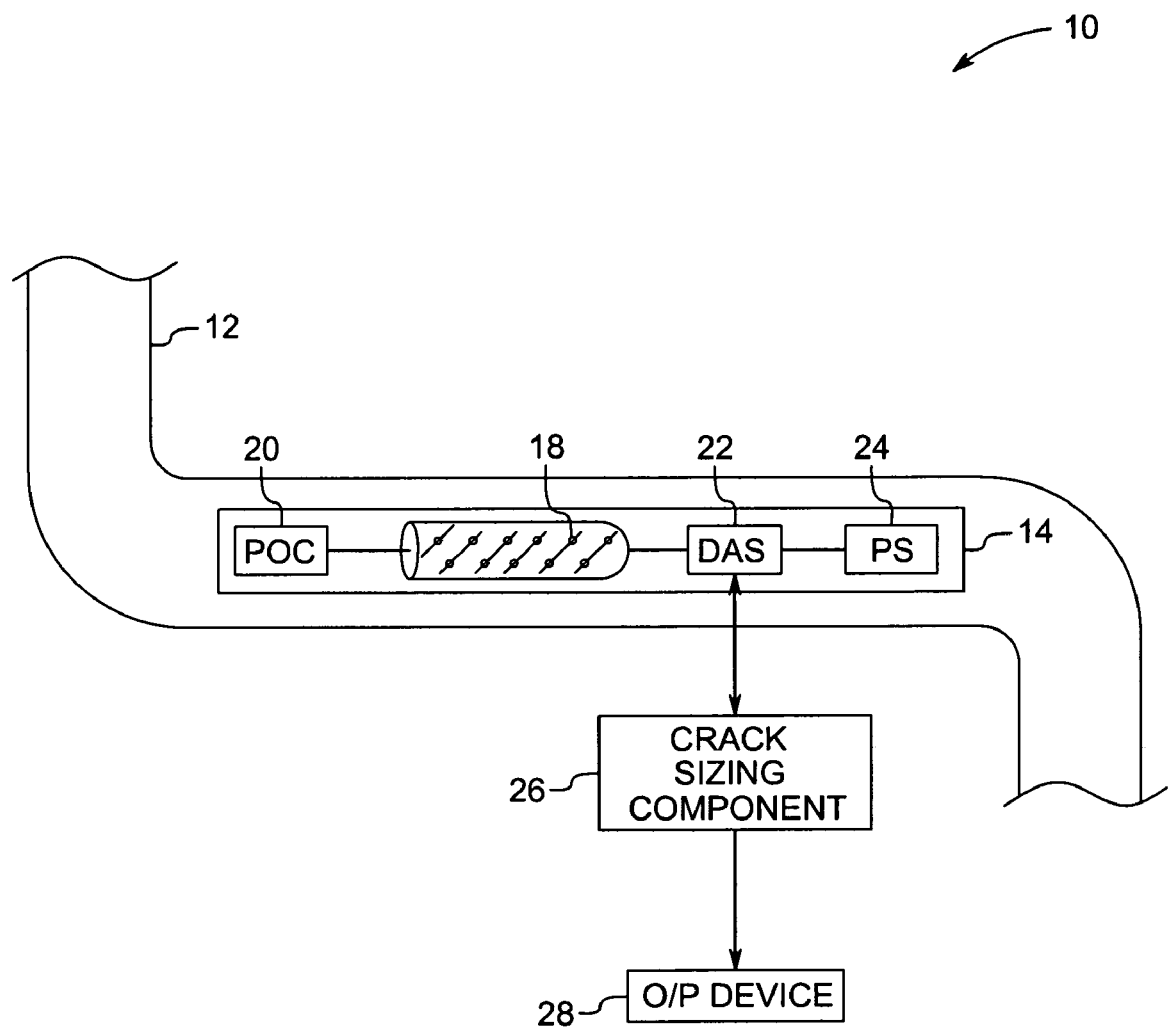
FIG. 1 is a block diagram showing a pipeline inspection system according to aspects of the present technique.

FIG. 1 is a block diagram showing a pipeline inspection system, designated generally by reference numeral 10. The pipeline inspection system 10 includes a pipeline 12 and a pipeline inspection gage (PIG) 14. The PIG 14 is a scanning device placed inside the pipeline and is typically used to find flaws such as cracks in the walls of the pipeline 12. The PIG 14 is transported through the length of the pipeline along with the fluid flow in the pipeline. The PIG is typically configured to send ultrasonic signals circumferentially in the pipeline walls and to receive reflected signals within the pipeline walls. As shown in the FIG. 1, the PIG 14 includes multiple sensors 18. The sensors 18 are typically transducers that function as transmitters and receivers of ultrasonic signals. The sensors 18, which may be configured to keep a fixed distance from the internal surface of the pipeline, may be piezoelectric sensors or other sensors suitable for this type of application. The PIG 14 also includes a positional component (POC) 20, which determines the position and orientation of the PIG 14 in the pipeline. The PIG 14 further includes a data acquisition system (DAS) 22 for receiving the data acquired by the sensors 18. A power source (PS) 24 provides power to sensors 18, the POC 20, the DAS 22 and other associated components in the PIG 14. It would be understood by those skilled in the art that the PIG 14 may have additional components such as an onboard clock for time stamping each record as acquired by the DAS or the like.

The pipeline inspection system 10 also includes a crack sizing component 26 which may be incorporated inside the PIG 14 or may be located remotely. The crack sizing component 26 is used for estimating the depth of the crack using data from multiple sensors, according to aspects of the present technique, as described in more detail in reference to FIGS. 2-5. The pipeline inspection system may also be coupled to an output (O/P) device 28, for example an offline computer system for display of results from the post-processing component and for providing external inputs including user/operator inputs.

Aspects of the present technique use the ultrasonic ray tracing approach. Ray tracing simulates ultrasound beam propagation in the pipe walls. This simulation is used to estimate the location of the reflector in actual B-scans and A-scans. As is well understood by those skilled in the art, B-scan in ultrasound refers generally to the signal received by a sensor over a spatial scan line, and A-scan refers generally to the signal received by the sensor at any particular position. In inspections, which are performed off-line, the component can be scanned with manual dexterity in two dimensions and crack tips located. In pipeline inspections, the present technique uses the discrete spatially distributed sensors in lieu of a circumferential scan while the PIG motion provides the axial scan.

Figure 2:
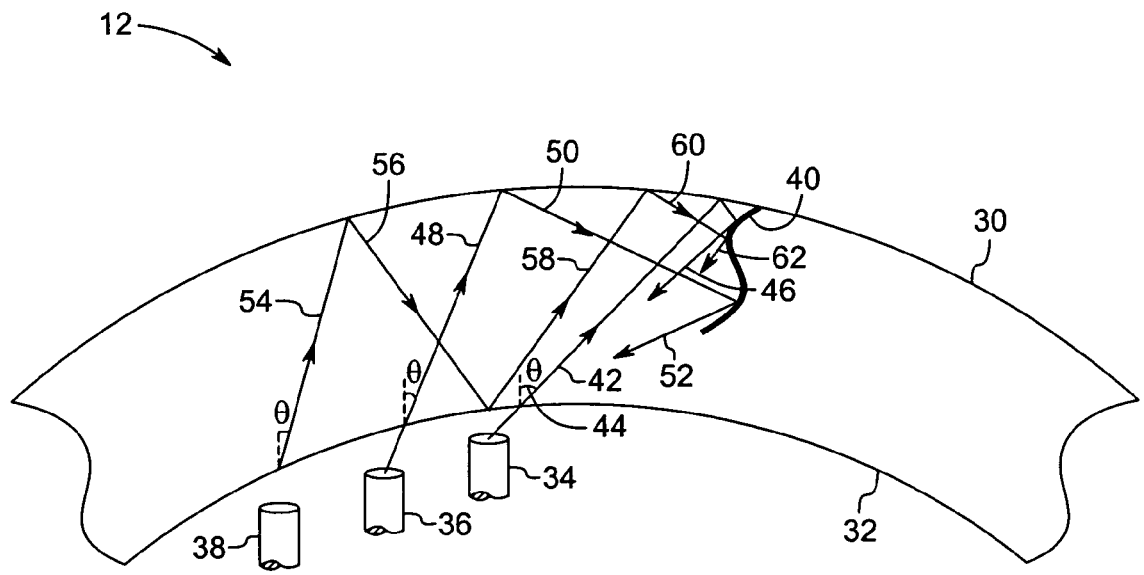
FIG. 2 is a cross-sectional view of the pipeline of FIG. 1 showing a crack on a surface of the pipeline and multiple sensors disposed around the pipeline for sending and receiving the ultrasound signals according to aspects of the present technique.

FIG. 2 is a cross-sectional view of the pipeline 12 of FIG. 1 showing an axial crack 40 on an external surface 30 of a pipeline and multiple sensors (34, 36, 38) in the vicinity of the crack 40. Multiple sensors are disposed around the pipeline (by being positioned around a PIG, in this specific example)for sending and receiving the ultrasound signals. Ultrasonic shear waves may be employed in one example, which may be generated in the pipe wall by oblique incidence of the transmitted ultrasonic pulses through a liquid medium (for example, oil or water). The same sensor (transducer) may be used for both sending and receiving ultrasound signals, for example using pulse-echo technique. The pulse echo technique is an ultrasound method based on transmission of ultrasound pulses and detection of the echoes by the same transducer.

In the illustrated example, sensors 34, 36 and 38 are arranged such that the ultrasonic rays 42, 48 and 54 respectively strike the pipeline at a known angle θ. These rays travel to the pipeline surface and may be reflected back, as shown generally by the paths indicated by reference numerals 46, 52, and 62 or re-transmitted, as shown by paths 50, 56, 58 and 60. The information obtained from these sensors, which sense the presence of the crack from discrete spatial locations around the crack, is used for detection and sizing of cracks. In the illustrated example, sensor 34 is placed at 0.5 skip distance from the root of the crack 40. Skip distance is the distance between the internal surface and external surface of the pipeline, measured at a predetermined angle. In one example the angle used for computing the skip distance was 45 degrees. In the illustrated example, the sensor 38 is located 1.0 skip distance from the sensor 34, and the sensor 36 is located such that it receives a significant reflection from a region of the crack 40, which is favorably oriented. Any reflected signal received from the root of the crack is generally a strong signal and is useful in estimating the depth of the crack. In the illustrated example, the sensor 36 receives a reflected signal from near the root of the crack 40. The estimated depth of the crack in the illustrated example is the maximum depth of reflecting point on the crack, as captured from different sensors (34, 36, and 38) around the crack under consideration.

Again, the presence of a crack may be identified with respect to the origin of crack in the external surface 30 (half skip distance) or the internal surface 32 (full skip distance). The skip distance is useful in determining whether the sensor is receiving a signal from a crack in the external surface or internal surface of the pipeline.

Figure 3:
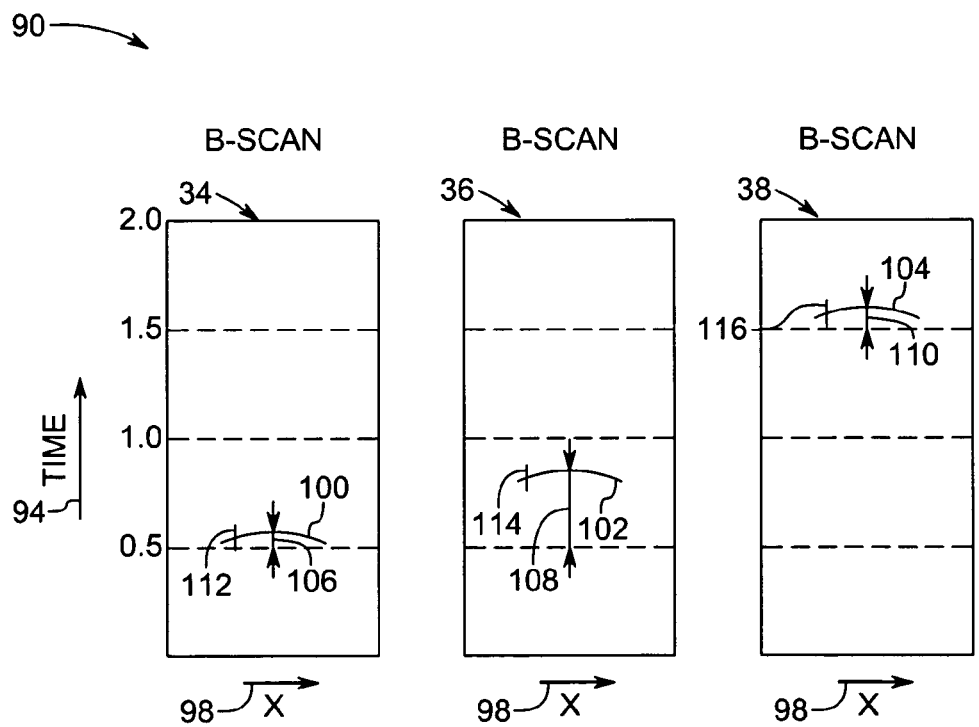
FIG. 3 is a graphical representation of exemplary scan data as obtained in B-scans and corresponding to reflected signals from a crack according to aspects of the present technique.

FIG. 3 shows individual B-scans for the three sensors 34, 36, and 38 as the PIG 14 (FIG. 1) moves through the pipeline 12. As the PIG 14 moves along the pipeline 12, different sensors view the crack 40 (FIG. 2) and corresponding B-scans are obtained. Arrows 98 indicate the odometer position with respect to time shown on y-axis and denoted generally by reference numeral 94. The odometer position reflects how far the PIG has traveled in the pipeline and is indicated in kilometers. Indications 100, 102, 104 are the signal responses received by the sensors 34, 36 and 38 respectively, from the crack shown in FIG. 2. The distance indicated by reference numerals 106, 108 and 110 is an indicator of the maximum depth of the crack as seen by individual sensors, and is calculated by using the skip distance values (0.5, 1.0, 1.5 and 2.0), according to aspects of the present technique. In practice, each point on the indications 100, 102, and 104 may be analyzed by using the respective A-scans to get the accurate depth estimate. For example, points indicated generally by reference numerals 112, 114, and 116 may be viewed as A-scans for more information as discussed in reference to FIG. 4

Figure 4:
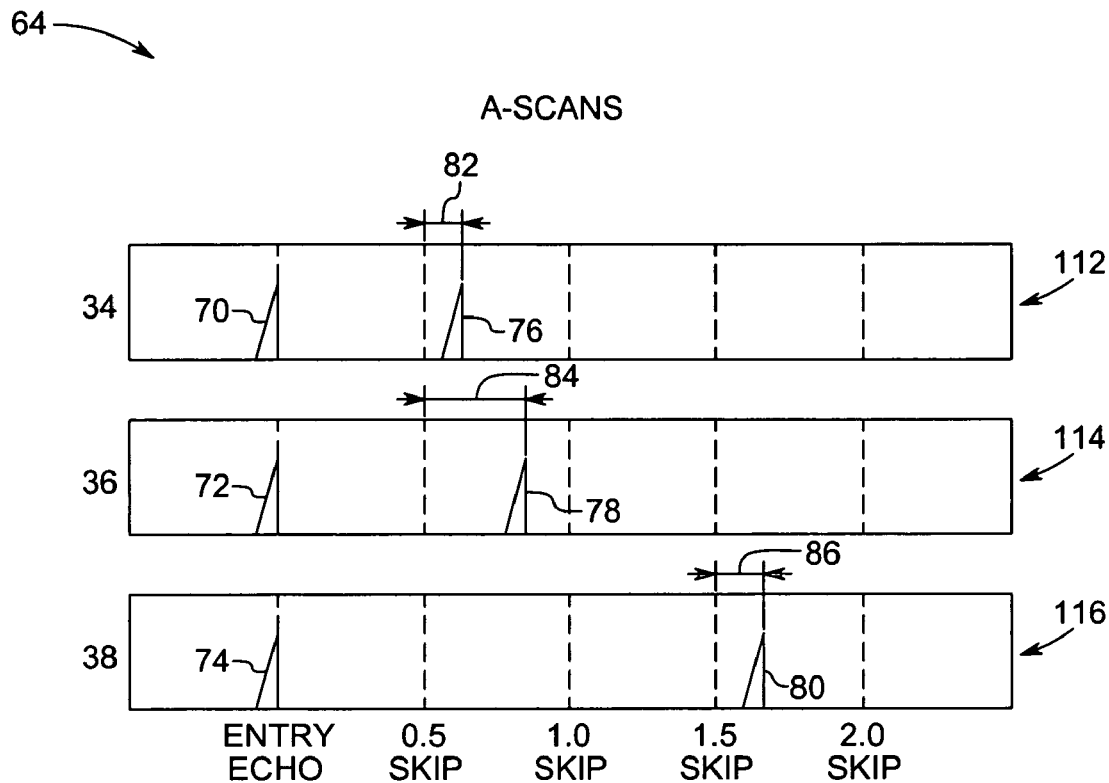
FIG. 4 is a graphical representation of exemplary scan data obtained in A-scans and corresponding to certain points in the B-scans of FIG.3 for three discrete sensors according to aspects of the present technique.

FIG. 4 is a diagrammatic representation of A-scans denoted generally by reference numeral 64 for the sensors 34, 36 and 38 shown in FIG. 2. The A-scans are shown corresponding to points 112, 114, and 116 in FIG. 3 with respect to skip distance (entry echo, 0.5 skip, 1.0 skip, 1.5 skip and 2.0 skip). According to aspects of the present technique, any signal response after entry echo and between 0.5 skip distance intervals is an indication of a flaw. Thus, the spikes 76, 78, 80 are an indication of a flaw in the pipeline surface. The distances 82, 84 and 86 are computed using geometric parameters, time of flight and skip distance values. Maximum depth value as observed by each individual sensor is then calculated using these computations from individual A-scans, according to aspects of the present technique. Then the maximum depth value from amongst all the sensors is selected as the estimated depth of the crack, according to aspects of the present technique.

Thus, for calculating the depth estimate, the technique described herein uses parameters such as axial position of sensors, time of flight (ToF), which is sound propagation time from the pipeline surface to the reflector/flaw and back, and entry echo time, which indicates the beginning of travel of the ultrasonic signal from the surface of the pipeline. Further, geometric parameters may also be used to compute the half skip value, where this skip value is also used in the computation of the depth value of the crack.

Figure 5:
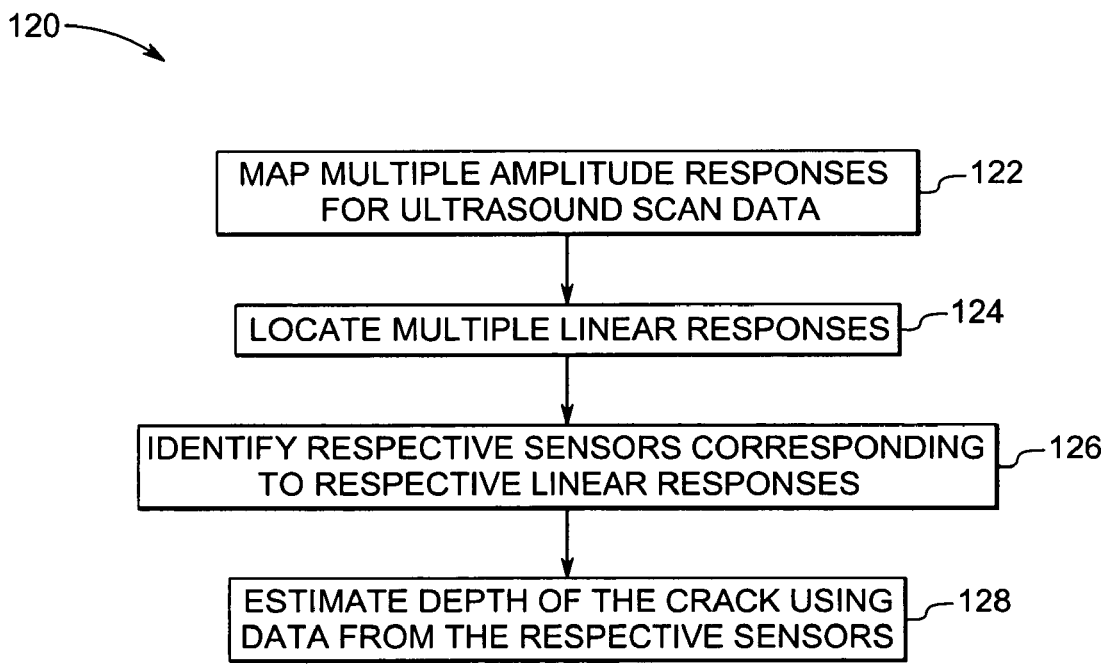
FIG. 5 is a flowchart illustrating exemplary steps for a method of inspecting cracks in a pipeline according to aspects of the present technique.

FIG. 5 is an illustrative flowchart 120 showing exemplary steps in accordance with aspects of the present techniques. Step 122 represents mapping multiple amplitude responses for ultrasound scan data received from multiple sensors around any object, e.g. a pipeline. As will be well appreciated by those skilled in the art, each mapped amplitude response is representative of a signal from one of the sensors. Mapped amplitude responses may be obtained using commercially available software. At step 124, a user (data analyst), or an automated alternative for example, a software program may observe the B-Scans of a given area in the data analysis software and determine prominent linear indications (multiple linear responses), which match with typical signatures of cracks, or crack-like flaws and notch-like flaws. Each linear response is typically an indicator of a reflected signal from the crack. If the linear indications show the characteristic response of any of the flaw categories, then the information on individual tracks is captured. That information may include, for example, the amplitude of the response and the skip distance. Thus, at step 126, respective sensors corresponding to respective linear responses are identified. The data, for example, the position, sensor number and time-of-flight value for each point in the linear indication, as shown in the B-Scan of FIG. 3, is obtained with respect to these sensors. The data may also be conditioned to remove certain noise parameters. In one example, the information related to wall thickness, pipe diameter, ultrasound velocity in medium, axial position, entry echo time for all A Scans and raw B Scan data for all sensors, may also be extracted from the data file. It may be noted that the accuracy of estimating the depth of crack may be greater when the number of sensors receiving the signal from the crack is more. Also some sensors provide more useful information about the depth estimate, for example, the sensors capturing information from the root (or tip) of the crack. Then by using position, skip distance values, time of flight and entry echo time the depth values may be computed, as indicated at step 128. The reported depth value is the depth estimate for the identified point in B Scan. In one example, the analysis may be done point by point until all the points corresponding to the linear indication are covered. In another example, the coordinates of all the points in the track may be provided followed by sequential execution of the technique. Also, for each track the reported output may be the maximum depth estimate from all points in the track. Alternately, the reported output may be the average depth estimate of the crack. The computation of the maximum depth estimate or the average depth estimate may be accomplished by considering all sensors around the flaw under consideration.

It would be well appreciated by those skilled in the art that the foregoing flowchart shows the functionality and operation of one embodiment in accordance with aspects of the present technique with respect to a pipeline. In this regard, each block/component represents a module, segment, or portion of code, which comprises one or more executable instructions for implementing the specified logical function(s). It should also be noted that in some alternative implementations, the functions noted in the blocks may occur out of the order noted in the figures or, for example, may in fact be executed substantially concurrently or in the reverse order, depending upon the functionality involved. Also, one of ordinary skill in the art will recognize that additional blocks may be added. Furthermore, the functions can be implemented in programming languages such as C++, MATLAB, or JAVA; however, other languages can be used.

The various embodiments and aspects of the invention described above may facilitate the creation of an ordered listing of executable instructions for implementing logical functions. Such an ordered listing can be embodied in any computer-readable medium for use by or in connection with a computer-based system that can retrieve the instructions and execute them. In the context of this application, the computer-readable medium can be any means that can contain, store, communicate, propagate, transmit or transport the instructions. The computer readable medium can be an electronic, a magnetic, an optical, an electromagnetic, or an infrared system, apparatus, or device. An illustrative, but non-exhaustive list of computer-readable mediums can include an electrical connection (electronic) having one or more wires, a portable computer diskette (magnetic), a random access memory (RAM) (magnetic), a read-only memory (ROM) (magnetic), an erasable programmable read-only memory (EPROM or Flash memory) (magnetic), an optical fiber (optical), and a portable compact disc read-only memory (CDROM) (optical).

Note that the computer readable medium may comprise paper or another suitable medium upon which the instructions are printed. For instance, the instructions can be electronically captured via optical scanning of the paper or other medium, then compiled, interpreted or otherwise processed in a suitable manner if necessary, and then stored in a computer memory.

It will also be well appreciated by those skilled in the art that the techniques described herein may be incorporated as algorithms, or could be implemented through hardware, for example, by using a programmed chip. Again, the algorithm or the hardware implementation may be incorporated in the PIG or may be a part of a remote processing system.

The aspects of the present technique as described herein have several advantages over existing flaw detection and depth estimation techniques. Some of the advantages may include an increase in the accuracy of crack depth estimation, reduction of manual analysis of crack depths and providing automation for depth estimation. Aspects of the present technique also help in reducing subjectivity and operator dependence, and decreasing reporting time. Thus, aspects of the present technique address the crack depth estimation problem in pipelines and provide an automated sizing method, where analyst intervention is not required in depth computation.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for estimating a depth of a crack from ultrasound scan data, the method comprising:
    mapping a plurality of amplitude responses from the ultrasound scan data, each mapped amplitude response being representative of a signal from one of a plurality of sensors;

locating a plurality of linear responses among the plurality of mapped amplitude responses, each linear response being an indicator of a reflected signal from the crack;

identifying one or more sensors corresponding to the linear responses from the crack;

estimating the depth of the crack using data from the one or more sensors; and determining whether the crack originates on an external surface or an internal surface of a pipeline.

2. The method of claim 1, wherein data from the plurality of sensors comprises data for position, time of flight and entry echo time of the sensor signal.

3. The method of claim 1, comprising computing a maximum depth estimate for the crack using the data from each of the plurality of sensors receiving the reflected signal from the crack.

4. The method of claim 1, comprising computing an average depth estimate for the crack using the data from each of the plurality of sensors receiving the reflected signal from the crack.

5. The method of claim 1, comprising using a skip distance value for the respective sensors for estimating the depth of the crack.

6. The method of claim 1, wherein the signal comprises a central ray of an ultrasound beam.

7. An apparatus for estimating a depth of a crack from ultrasound scan data, the apparatus comprising:

an amplitude processor that is adapted to map a plurality of amplitude responses from the ultrasound scan data, and to locate a plurality of linear responses, each mapped amplitude response being representative of a respective sensor signal, and each linear response being an indicator of a reflected signal from the crack; and a crack sizing component that is adapted to identify respective sensors corresponding to respective linear responses and to estimate the depth of the crack using data from the respective sensors, and wherein the crack sizing component is further adapted to determine whether the crack originates on an external surface or an internal surface of a pipeline.

8. The apparatus of claim 7, wherein data from the respective sensors comprises data for position, time of flight and entry echo time of the sensor signal.

9. The apparatus of claim 7, wherein the crack sizing component is configured to compute a maximum depth estimate for the crack using the data from each of a plurality of sensors receiving the reflected signal from the crack.

10. The apparatus of claim 7, wherein the crack sizing component is configured to compute an average depth estimate for the crack using the data from each of a plurality of sensors receiving the reflected signal from the crack.

11. The apparatus of claim 7, wherein the crack sizing component uses a skip distance value for the respective sensors for estimating the depth of the crack.

12. An ultrasound imaging system, comprising:

a plurality of sensors disposed at discrete spatial distances along an object being inspected, each of the sensors being configured to transmit to and receive signals from the object;

a data acquisition system that is adapted to acquire ultrasound scan data from the plurality of sensors, the data being representative of signals received by the plurality of sensors;

an amplitude processing component that is adapted to map a plurality of amplitude responses from the ultrasound scan data, and to locate a plurality of linear responses, each mapped amplitude response representing a respective sensor signal, and each linear response indicating a reflected signal from a crack in the object; and a crack sizing component that is adapted to identify respective sensors corresponding to respective linear responses and to estimate a depth of the crack using data from the respective sensors, and wherein the crack sizing component is further adapted to determine whether the crack originates on an external surface or an internal surface of a pipeline.

13. The imaging system of claim 12, wherein data from the plurality of sensors comprises data for position, time of flight and entry echo time of the sensor signal.

14. The imaging system of claim 12, wherein the crack sizing component is configured to compute a maximum depth estimate for the crack using the data from each of the plurality of sensors receiving the reflected signal from the crack.

15. The imaging system of claim 12, wherein the crack sizing component is configured to compute an average depth estimate for the crack using the data from each of the plurality of sensors receiving the reflected signal from the crack.

16. The imaging system of claim 12, wherein the crack sizing component uses a skip distance value for the respective sensors for estimating the depth of the crack.

\* \* \* \* \*